(12) United States Patent
Chou

(10) Patent No.: US 8,797,514 B2
(45) Date of Patent: Aug. 5, 2014

(54) LOCALIZED DYNAMIC LIGHT SCATTERING SYSTEM WITH DOPPLER VELOCITY MEASURING CAPABILITY

(71) Applicant: Lidek Chou, Pleasanton, CA (US)

(72) Inventor: Lidek Chou, Pleasanton, CA (US)

(73) Assignee: Lidek Chou, Pleasanton, CA (US)

( * ) Notice: Subject to any disclaimer, the term of this patent is extended or adjusted under 35 U.S.C. 154(b) by 144 days.

(21) Appl. No.: 13/674,110

(22) Filed: Nov. 12, 2012

(65) Prior Publication Data
US 2014/0132943 A1    May 15, 2014

(51) Int. Cl.
*G01P 3/36* (2006.01)
*G01N 15/02* (2006.01)
*G01N 21/49* (2006.01)

(52) U.S. Cl.
CPC *G01N 21/49* (2013.01); *G01P 3/36* (2013.01); *G01N 15/0211* (2013.01)
USPC ......... 356/28.5; 356/4.09; 356/35.5; 356/450

(58) Field of Classification Search
CPC ........ G01C 3/08; G01C 15/002; G01S 17/89; G01S 7/4817; G01S 17/42
USPC ......... 356/3.01, 4.01, 4.07, 5.01, 5.09, 9, 625
See application file for complete search history.

(56) References Cited

U.S. PATENT DOCUMENTS

2001/0028679 A1 * 10/2001 Chou ............................ 375/226
2010/0231909 A1 *  9/2010 Trainer ......................... 356/336

\* cited by examiner

*Primary Examiner* — Isam Alsomiri
*Assistant Examiner* — Samantha K Abraham

(57) ABSTRACT

A localized dynamic light scattering measurement system includes a beam displacer for splitting an incident beam having two orthogonal linearly polarized beam components with slightly different frequencies into two orthogonal linearly polarized output beams focused onto an object to be measured. The beam displacer cooperates with an iris to collect and recombine scattering beams each reversely backscattered at 180 degrees from the object so as to form a signal beam, which is polarized by a polarizer to produce two polarization components, thereby generating a heterodyne interference signal associated with the polarization components. A signal processing unit obtains measurement data on the object based on power spectrum or autocorrelation data corresponding to the heterodyne interference signal.

12 Claims, 7 Drawing Sheets

LOCALIZED DYNAMIC LIGHT SCATTERING SYSTEM WITH DOPPLER VELOCITY MEASURING CAPABILITY

BACKGROUND OF THE INVENTION

1. Field of the Invention

The invention relates to dynamic light scattering, and more particularly to a localized dynamic light scattering measurement system.

2. Description of the Related Art

Laser Doppler velocimetry (LDV) is a well known technique for contactless measurement of the speed and direction of an object in motion, as well as the flow velocity of liquid materials. The motion of a solid object is easy to detect and measure. However, accurate measurements of fluid flow velocity are relatively difficult. Similar to an LDV system, which is used to detect and measure velocity of motions, a dynamic light scattering (DLS) system is also used to characterize motion of particles. But unlike in an LDV system, in which the signal measured is deterministic, the light scattering signal in DLS is a stochastic process that can only be described statistically. Based on detection and measurement of single Rayleigh scattered light from an ensemble of small particles, DLS is a powerful technique to observe the dynamics of particles or molecules undergoing Brownian motion. The dynamic information of these particles can be derived using either autocorrelation or the power spectrum of the intensity time trace signal. The characteristic time of the autocorrelation function or the width of the power spectrum is used to determine the diffusion coefficient of particles in a solution that is proportional to the size of the particles. However, in order to properly extract the dynamic information, assumption of light undergone a limited number of scattering events needs to be satisfied, meaning that each detected photon has been scattered by the sample under a limited number of scattering. Multiple scattering is often encountered in real life situation however, for example, light scattering in tissues. It would be difficult to accurately interpret the dynamic information of a sample if the degree of multiple scattering is severe enough.

FIG. 1 illustrates a conventional dynamic light scattering system proposed in an article by S. Sudol, Y. Miyasaka, K. Otsuka, Y. Takahashi, T. Oishi, and J.-Y. Ko, entitled "Quick and easy measurement of particle size of Brownian particles and planktons in water using a self-mixing laser," Optics Express, vol. 14, no. 3, pp. 1044-1054, February 2006 The conventional dynamic light scattering system is used to measure the size of particles 84 in Brownian motion, and includes a laser source 81, a beam splitter 82, two acousto-optic modulators (AOMs) 83, a photodetector 85, and a spectrum analyzer 86. The laser source 81 produces a laser beam having an angular frequency at $\omega_0$. Almost all the laser beam is transmitted through the beam splitter 82, is then frequency-shifted by the AOMs 83, and is focused onto an object 84 to be measurement containing small particles in suspension by a focusing lens (not shown) such that changing the modulation frequencies of the two AOMs 83 produces a shift of $\Delta\omega$ in the carrier frequency at the end of the round-trip. The photodetector 85 receives the rest of the laser beam reflected by the beam splitter 82 and scattered light fed from the moving particles to the laser source 81 to produce an interference signal in the form of an electrical signal that is fed to the spectrum analyzer 86. As such, a power spectrum corresponding to the electrical signal and having a central frequency at $\Delta\omega$ is acquired to have a Lorentz profile. The width of the power spectrum is used to determine the diffusion coefficient of the particles that is proportional to the size of the particles. In this case, the self-mixing laser is used.

The self-mixing laser can also be applied to an LDV system. Since Doppler shift is directly proportional to a component of the motion velocity of the object 84 in the direction of incident light, i.e., object motion along the direction of the wave vector can only be measured using a single self-mixing laser, two self-mixing setups are required for measuring in-plane motions of the objects 84. If only a single laser source is utilized for self-mixing, there are multiple beam splitters and multiple pairs of the AOMs 83 required, thereby increasing the overall complexity and loss of light intensity.

If motion/speed of the object 84 is very slow, Doppler shift becomes very small. In this case, interpretation of the center frequency of the power spectrum is difficult even though the power of the incident beam or the high detection sensitivity of the photodetector 85 is used.

Therefore, improvements may be made to the above techniques.

SUMMARY OF THE INVENTION

Therefore, an object of the present invention is to provide a localized dynamic light scattering measurement system that is capable of Doppler velocity or particle size measurements with high sensitivity.

According to the present invention, a localized dynamic light scattering measurement system comprises a two-frequency laser source, a beam splitter, an iris, a beam displacer, a focusing lens unit, a polarizer, a photo detecting unit, and a signal processing unit.

The two-frequency laser source produces an input laser beam propagating along an optical axis and composed of orthogonal linearly polarized first and second beam components with slightly different frequencies.

The beam splitter is disposed on the optical axis for transmitting a portion of the input laser beam produced by the two-frequency laser source such that the portion of the input laser beam transmitted by said beam splitter serves as an incident beam.

The beam displacer splits the incident beam into orthogonal linearly polarized first and second output beams corresponding respectively to the first and second beam components. The orthogonal linearly polarized first and second output beams are parallel to the incident beam and are spaced apart from each other by a predetermined spacing upon exiting the beam displacer.

The focusing lens unit focuses the orthogonal linearly polarized first and second output beams onto an object to be measured, and collects light backscattered from the object upon the orthogonal linearly polarized first and second output beams striking the object.

The iris is disposed between the beam splitter and the beam displacer, and has an opening aligned with the optical axis for permitting the incident beam to pass through to limit a spot size of the incident beam.

The beam displacer serving as a polarization gate cooperates with the iris serving a spatial filter gate for collect and recombine scattering beams, each of which is reversely backscattered at 180 degrees from the object and corresponds to a specific portion of the light collected by the focusing lens unit so as to forma signal beam to be detected that passes through the opening in the iris.

The polarizer polarizes the signal beam from the iris to produce, along a polarization axis of the polarizer, first and second polarization components with common polarization.

The photo detecting unit receives the first and second common polarization components from the polarizer to detect and generate a heterodyne interference signal associated with the first and second polarization components, and converts the heterodyne interference signal into an electrical signal.

The signal processing unit is connected electrically to the photo detecting unit for receiving the electrical signal therefrom. The signal processing unit is operable to analyze the electrical signal received thereby to generate power spectrum data and autocorrelation data corresponding to the heterodyne interference signal and obtain measurement data on the object based on the power spectrum data or the autocorrelation data.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENT

Figure 1:
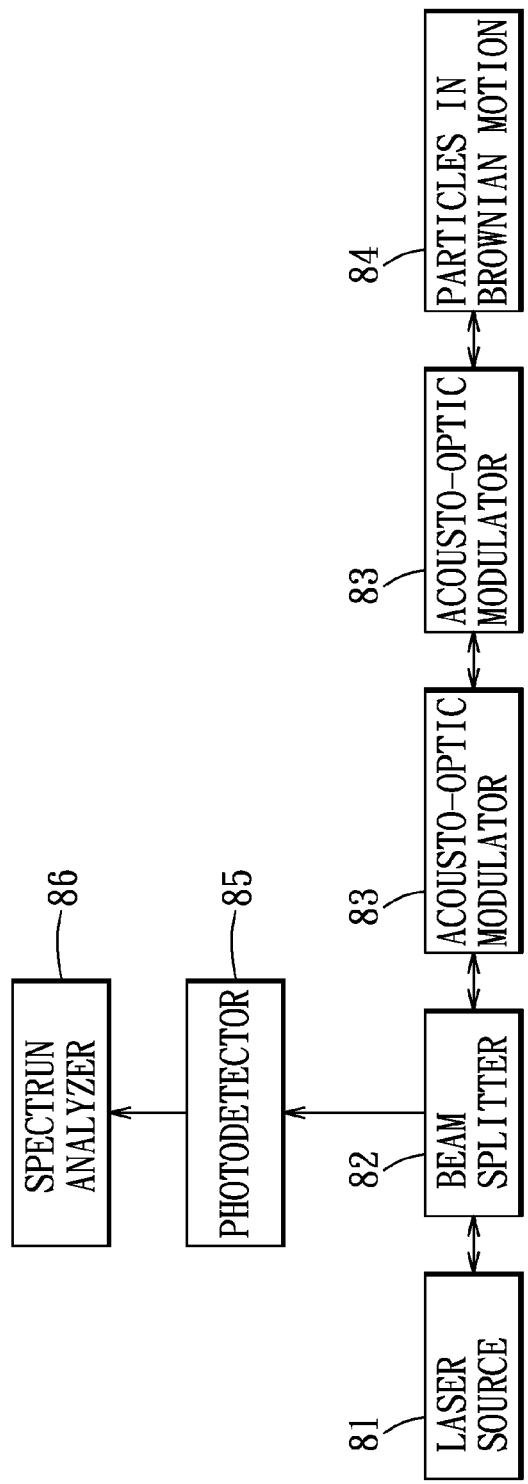
FIG. 1 is a schematic block diagram illustrating a conventional dynamic light scattering system.
Figure 2:
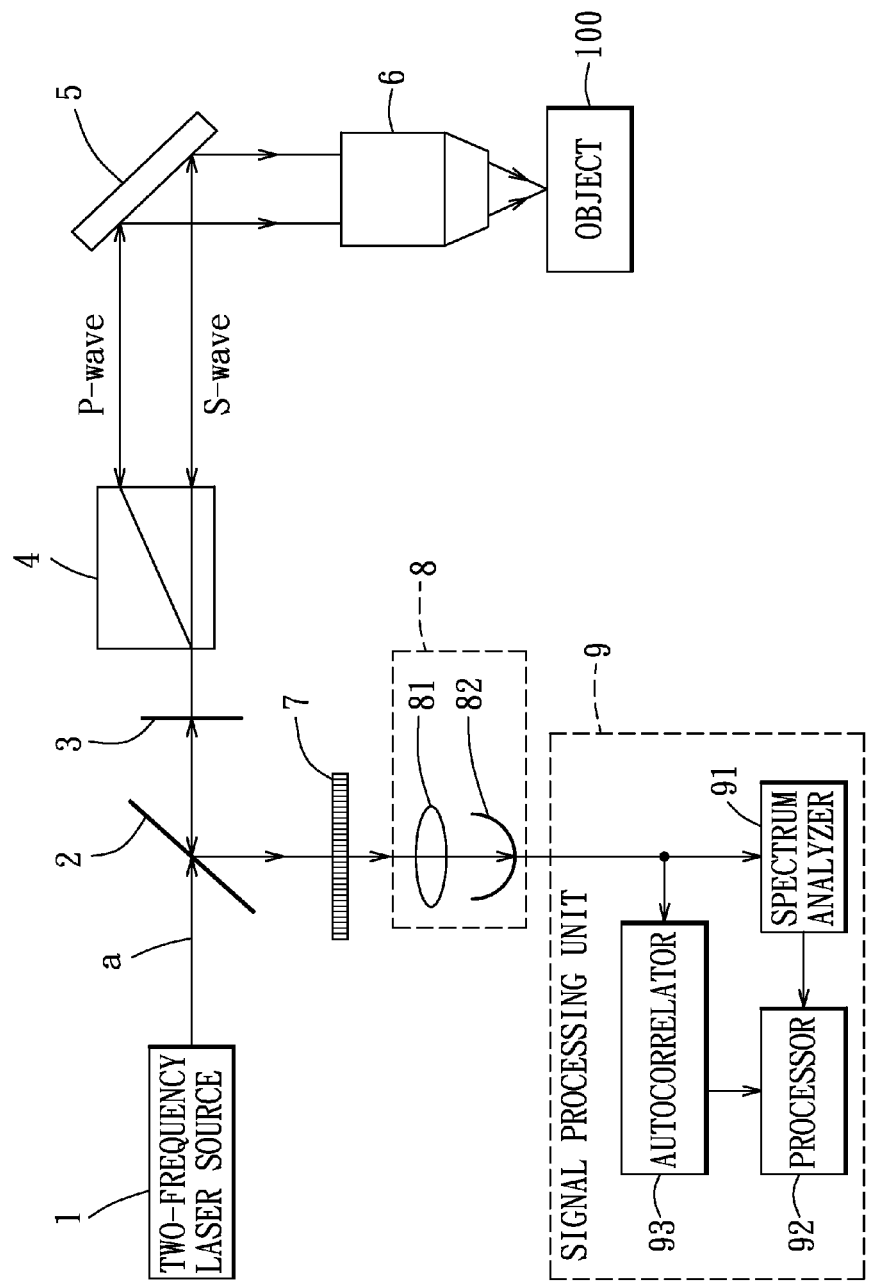
FIG. 2 is a schematic view illustrating the preferred embodiment of a localized dynamic light scattering measurement system according to the present invention.

Referring to FIG. 2, the preferred embodiment of a localized dynamic light scattering measurement system according to the present invention is shown to include a two-frequency laser source 1, a beam splitter 2, an iris 3, a beam displacer 4, a light reflector 5, a focusing lens unit 6, a polarizer 7, a photo detecting unit 8, and a signal processing unit 9.

Figure 2A:
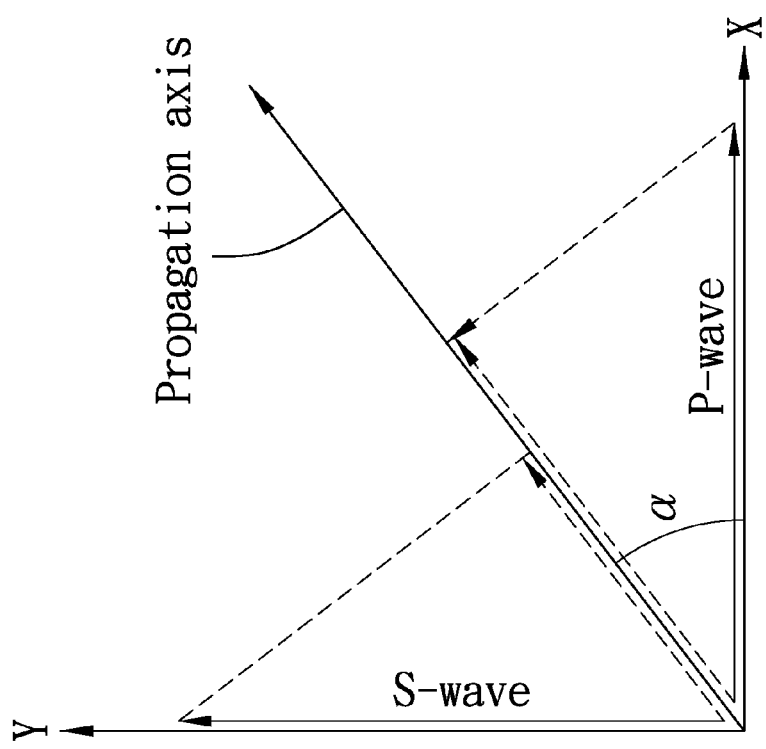
FIG. 2a illustrates orthogonal linearly polarized first and second beam components of an input laser beam produced by a two-frequency laser source of the preferred embodiment.

The two-frequency laser source 1 produces an input laser beam propagating along an optical axis (a). The input laser beam is composed of orthogonal linearly polarized first and second beam components with slightly different frequencies. In this embodiment, as shown in FIG. 2a, the orthogonal linearly polarized first and second beam components correspond respectively to horizontally polarized and vertically polarized waves, such as P-wave and S-wave in an incident plane, which is defined by a Y-axis and a propagation axis. The propagation axis is oriented at an angle ($\alpha$) with an X-axis. The angular frequencies of the first and second beam components are indicated by $\omega_p$ and $\omega_s$, respectively.

The beam splitter 2 is disposed on the optical axis (a) for transmitting a portion of the input laser beam produced by the two-frequency laser source 1 such that the portion of the input laser beam transmitted by said beam splitter 2 serves as an incident beam traveling along the optical axis (a). In this embodiment, half of the input laser beam is transmitted through the beam splitter 2, but is not limited to this.

The iris 3 is disposed on the optical axis (a), and having an opening 31 aligned with the optical axis (a) for permitting the incident beam to pass through to limit a spot size of the incident beam.

Figure 3:
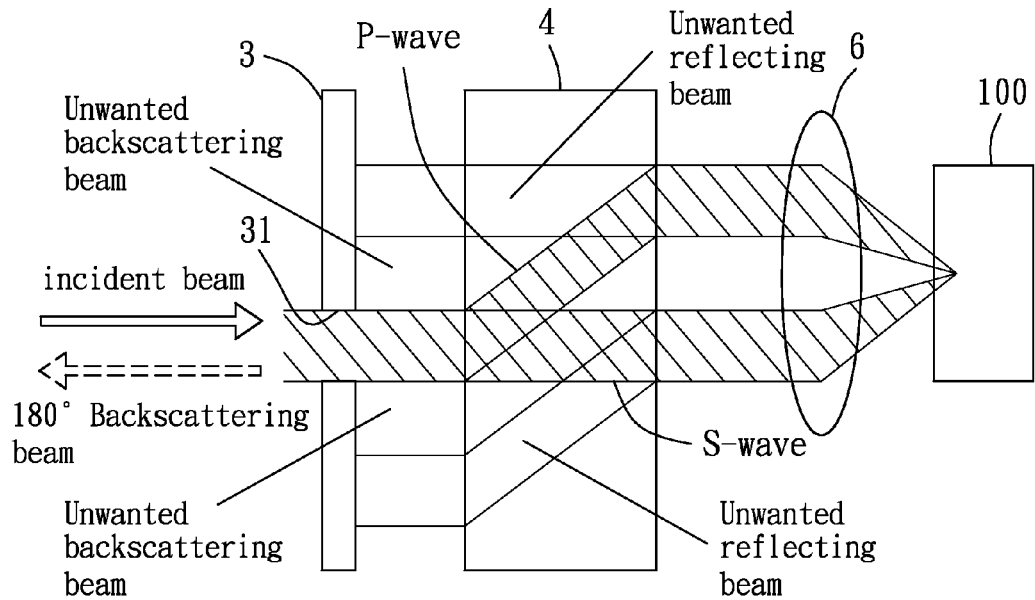
FIG. 3 is a schematic view illustrating how a beam displacer and an iris of the preferred embodiment filters unwanted backscattering and reflecting beams.

The beam displacer 4 is placed so that the iris 3 is disposed between the beam splitter 2 and the beam displacer 4. In this embodiment, the beam displacer 4 is a uniaxial birefringence crystal prism for splitting the incident beam into orthogonal linearly polarized first and second output beams corresponding respectively to the first and second beam components such that the angular frequencies of the orthogonal linearly polarized first and second output beams are indicated by $\omega_p$ and $\omega_s$, respectively. The orthogonal linearly polarized first and second output beams are parallel to the incident beam and are spaced apart from each other by a predetermined spacing, for example 4 mm, upon exiting the beam displacer 4. More specifically, as best shown in FIG. 3, the second output beam, i.e., the S-wave, passes straight through the beam displacer 4, while the first output beam, i.e., the P-wave, transmits through the beam displacer 4 at an angle with respect to the second output beam. Then, both the orthogonal linearly polarized first and second output beams exit the beam displacer 4 in a parallel fashion.

The orthogonal linearly polarized first and second output beams are reflected by the light reflector 5 toward the focusing lens unit 6. In this embodiment, the light reflector 5 is a mirror. In other embodiments, the light reflector 5 can be omitted when the orthogonal linearly polarized first and second output beams are directly received by the focusing lens unit 6.

The focusing lens unit 6 focuses the orthogonal linearly polarized first and second output beams onto an object 100 to be measured, and collects light backscattered from the object 100 upon the orthogonal linearly polarized first and second output beams striking the object 100. In this embodiment, the focusing lens unit 6 is a microscope objective.

It is noted that the beam displacer 4 serves as a polarization gate, and the iris 3 serves as a spatial filter gate such that the beam displacer 4 cooperates with the iris 3 to collect and recombine scattering beams each reversely backscattered at 180 degrees from the object 100 and corresponding to a specific portion of the light collected by the focusing lens unit 6 so as to form a signal beam to be detected that passes through the opening 31 in the iris 3. In addition, the scattering beams respectively propagate in 180-degree reverse directions of the orthogonal linearly polarized first and second output beams, and finally are coaxially recombined by the beam displacer 4 after passing the beam displacer 4 to pass through the opening 31 in the iris 3, thereby forming the signal beam.

Referring further to FIG. 3, the iris 3 serving as a spatial filter gate is also used to block unwanted scattering beams corresponding to the remaining of the light collected by the focusing lens unit 6, and unwanted reflecting beams reflected by the object 100 upon the orthogonal linearly polarized first and second output beams striking the object 100. The iris 3 permits the signal beam formed by the beam displacer 4 to propagate toward the beam splitter 2 through the opening 31 such that the signal beam is directed toward the polarizer 7 by the beam splitter 2.

Figure 4:
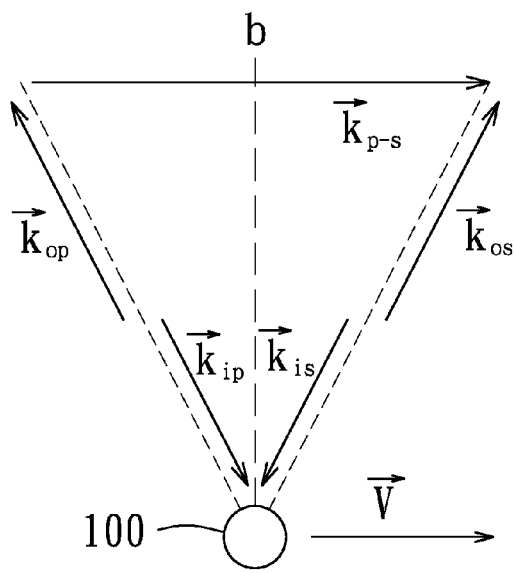
FIG. 4 is a schematic view illustrating relationship between orthogonal linearly polarized first and second output beams striking an object to be measured and two orthogonal linearly polarized scattering beams backscattered from the object.

Therefore, due to the presence of a combination of the iris 3 and the beam displacer 4, detection of undesirable signal can be suppressed, thereby enhancing the sensitivity of detection of a lateral Doppler signal, which corresponds to the velocity of motion parallel to $\vec{k}_{p-s}$ (see FIG. 4). In addition, since unwanted scattering light beams are effectively filtered out, Doppler broadening effect is reduced, thereby enhancing the sensitivity of detection on frequency shifted Doppler signal for velocity measurements.

The polarizer 7 polarizes the signal beam from the iris 3 to produce, along a polarization axis of the polarizer, first and second polarization components with common polarization. In this embodiment, the polarization axis of the polarizer 7 is oriented at 45° from the X-axis. The first and second polarization components correspond respectively to horizontally polarized and vertically polarized components of the signal beam.

The photo detecting unit 8 receives the first and second polarization components from the polarizer 7 to detect and generate a heterodyne interference signal associated with the first and second polarization components, and then converts the heterodyne interference signal into an electrical signal. In this embodiment, the photo detecting unit 8 includes a focusing lens 81, and a photodetector 82. The focusing lens 81 is used to focus the first and second polarization components from the polarizer 7 to the photodetector 82. The photodetector 82 receives the first and second polarization components focused by the focusing lens 81, and detects and generates a heterodyne interference signal associated with the first and second polarization components. Then, the photodetector 82 converts the heterodyne interference signal into the electrical signal. In this embodiment, the photodetector 82 is a photomultiplier tube, and the electrical signal is in the form of an electrical current.

The signal processing unit 9 is connected electrically to the photo detecting unit 8 for receiving the electrical signal therefrom. The signal processing unit 9 is operable to analyze the electrical signal received thereby to generate power spectrum data and autocorrelation data corresponding to the heterodyne interference signal and obtain measurement data on the object 100 based on the power spectrum data and the autocorrelation data. In this embodiment, the signal processing unit 9 includes a spectrum analyzer 91, an autocorrelator 93, and a processor 92. The spectrum analyzer 91 is connected electrically to the photodetector 82 of the photo detecting unit 8 for receiving the electrical signal therefrom. The spectrum analyzer 91 is operable to analyze the electrical signal to generate the power spectrum data corresponding to the heterodyne interference signal. The autocorrelator 93 is connected electrically to the photo detector 82 for receiving the electrical signal therefrom. The autocorrelator 93 is operable to analyze the electrical signal to generate the autocorrelation data corresponding to the heterodyne interference signal. The processor 92 is connected electrically to the spectrum analyzer 91 and the autocorrelator 93 for receiving the power spectrum data and the autocorrelation data therefrom. The processor 92 is operable to obtain measurement data on the object 100 based on the power spectrum data from the spectrum analyzer 91 or the autocorrelation data from the autocorrelator 93. In this embodiment, the processor 92 can be a CPU of a personal computer.

FIG. 4 illustrates relationship between the orthogonal linearly polarized first and second output beams striking the object 100 and two orthogonal linearly polarized 180-degree reverse backscattered beams from the object 100, where $\vec{k}_{ip}$ indicates a P-polarized incident wave vector corresponding to the first output beam, $\vec{k}_{is}$ indicates an s-polarized incident wave vector corresponding to the second output beam, $\vec{k}_{op}$ and $\vec{k}_{os}$ indicate P-polarized and S-polarized output wave vectors corresponding to the orthogonal linearly polarized 180-degree reverse backscattered beams from the object 100 and effectively passing through the beam displacer 4 and the iris 3, respectively, and $\vec{V}$ indicates a velocity vector of the object 100 in motion. Thus, angular frequencies ($\omega_p'$, $\omega_s'$) of the orthogonal linearly polarized 180-degree reverse backscattered beams are shifted from the center frequencies $\omega_p$, $\omega_s$ of the orthogonal linearly polarized first and second output beams, respectively. Due to Doppler shift induced by the moving object 100, the shifted angular frequencies ($\omega_p'$, $\omega_s'$) of the orthogonal linearly polarized 180-degree reverse backscattered beams can be expressed as following:

$$\omega_p' = \omega_p + (\vec{k}_{op} - \vec{k}_{ip})\vec{V}$$

$$\omega_s' = \omega_s + (\vec{k}_{os} - \vec{k}_{is})\vec{V}$$

Upon recombining and heterodyning of the two backscattered beams, the in-plane Doppler shift detected by the dual-polarization differential heterodyne method in this embodiment can be expressed as following:

$$\Delta\omega_{proposed} \equiv \omega_s' - \omega_p'$$
$$\Delta = \omega + [(\vec{k}_{os} - \vec{k}_{is}) - (\vec{k}_{op} - \vec{k}_{ip})] \cdot \vec{V}$$
$$\Delta = \omega + 2(\vec{k}_{ip} - \vec{k}_{is}) \cdot \vec{V}$$
$$\Delta = \omega + 2\vec{k}_{p-s} \cdot \vec{V}$$

where $\Delta\omega = \omega_p - \omega_s$ is the beat frequency of the two-frequency laser source 1. It is apparent that one of the main advantages of the localized dynamic light scattering measurement system is that a beat frequency of the same is centered at $\Delta\omega$. This allows easy directional detection of the object 100 in motion. Furthermore, the amount of Doppler shift detected by the dual-polarization differential heterodyne method in this embodiment is twice that detected by the conventional differential Doppler heterodyne technique. (Assuming the angle between two incident beams are the same for both methods.)

When the localized dynamic light scattering measurement system is used as a laser Doppler velocimeter for velocity measurement of the object 100 in motion, the power spectrum data generated by the signal processing unit 9 includes a Doppler shifted spectrum with a Doppler frequency.

If the object 100 is a solid sample, the measurement data obtained by the signal processing unit 9 includes a moving speed of the object 100 in a direction perpendicular to a bisector (b) of the orthogonal linearly polarized first and second output beams (see FIG. 4) focused by the focusing lens unit 6. The moving speed of the object 100 is determined based on the Doppler frequency of the Doppler shifted spectrum. In a first experiment of laser Doppler velocity measurement for a solid object in motion made by the preferred embodiment, the solid object is simulated by a circular rotation stage for 8 different rotational speed settings, wherein there are 4 distinct rotational speeds for each of clockwise (CW) and counterclockwise (CCW) directions of rotation: clockwise 20 deg/sec, 15 deg/sec, 10 deg/sec and 5 deg/sec, and counterclockwise 20 deg/sec, 15 deg/sec, 10 deg/sec and 5 deg/sec. Thus, the tangential velocity of the motorized rotation stage is regarded as the moving speed of the solid object. Table 1 shows experimental laser Doppler velocity measurement results of the first experiment. In Table 1, equivalent tangential velocities are calculated in accordance with the known rotational speeds and dimension of the rotation stage. This set of Doppler frequency data is acquired by locating the absolute maximum of spectrum.

TABLE 1

| Direction | Rotation speed setting (deg/sec) | Equivalent tangential velocity (mm/s) | Measured Doppler frequency (Hz) | Measured velocity (mm/s) | Error (%) |
| --- | --- | --- | --- | --- | --- |
| CW | 20 | −10.743 | −15690 | −10.552 | 1.78 |
| CW | 15 | −8.057 | −11830 | −7.956 | 1.26 |
| CW | 10 | −5.371 | −7800 | −5.246 | 2.34 |
| CW | 5 | −2.686 | −3860 | −2.596 | 3.34 |
| CCW | 5 | 2.686 | 4020 | 2.703 | 0.66 |
| CCW | 10 | 5.371 | 7800 | 5.246 | 2.34 |
| CCW | 15 | 8.057 | 11650 | 7.835 | 2.76 |
| CCW | 20 | 10.743 | 15850 | 10.659 | 0.78 |

Figure 5A:
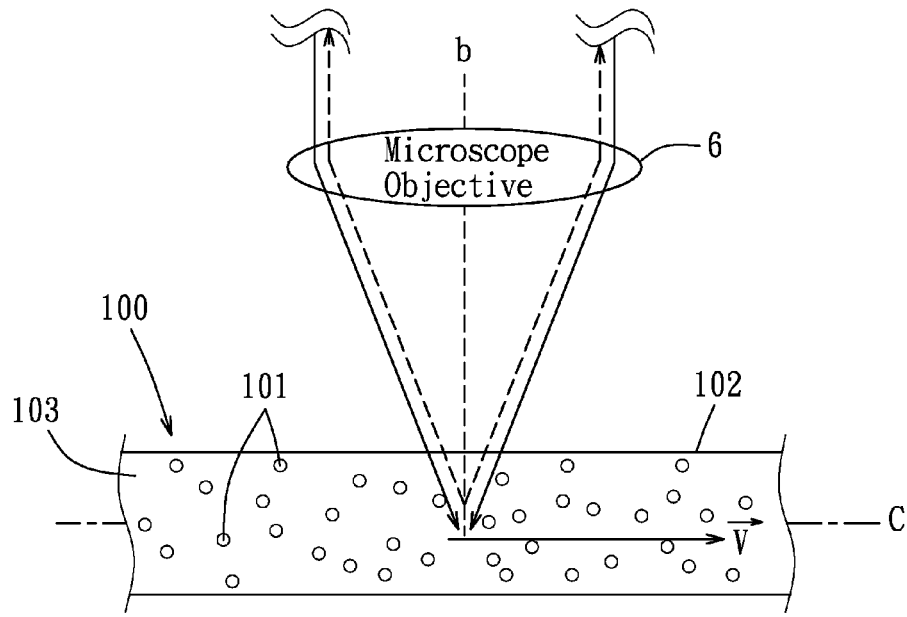
FIG. 5a is a fragmentary schematic view of the preferred embodiment when fluid flow of a flow tube is measured.

Referring further to FIG. 5a, if the object 100 is a flow tube that contains small particles 101 in liquid suspension 103 filled in a transparent capillary tube 102, which is oriented to be perpendicular to the bisector (b) of the orthogonal linearly polarized first and second output beams focused by the focusing lens unit 6, i.e., microscope objective, the measurement data obtained by the signal processing unit 9 includes a fluid flow velocity in the flow tube along a direction of a difference vector between a first incident wave vector corresponding to the first output beam and a second incident wave vector corresponding to the second output beam. The fluid flow velocity in the flow tube corresponds to a radial distance of a focal point of the orthogonal linearly polarized first and second output beams from a center axis (c) of the capillary tube 102. The fluid flow velocity in the flow tube is determined based on the Doppler frequency of the Doppler shifted spectrum. In a second experiment of fluid flow measurement for a flow tube made by the preferred embodiment using Doppler frequency measurement, sample fluid is filled into a syringe connected to the capillary tube 102 with an inner diameter around 700~800 μm through a flexible rubber tube. The sample fluid is then pumped by using a syringe pump to create liquid flow through the capillary tube 102. Test flow rate setting for this experiment are 0.14 ml/hr, 0.28 ml/hr, 0.42 ml/hr, 0.56 ml/hr and 0.70 ml/hr, and the direction of flow are the same for all settings. Table 2 shows experimental fluid flow measurement results of the second experiment.

TABLE 2

| Preset syringe pump flow rate (ml/hr) | Doppler frequency (Hz) | Estimated flow velocity (mm/s) | Estimated flow rate (ml/hr) |
| --- | --- | --- | --- |
| 0.14 | 119.0 | 52.3 | 0.08 |
| 0.28 | 507.6 | 223.1 | 0.35 |
| 0.42 | 812.7 | 357.2 | 0.57 |
| 0.56 | 1095.4 | 481.5 | 0.77 |
| 0.70 | 1398.5 | 614.8 | 0.98 |

Figure 5B:
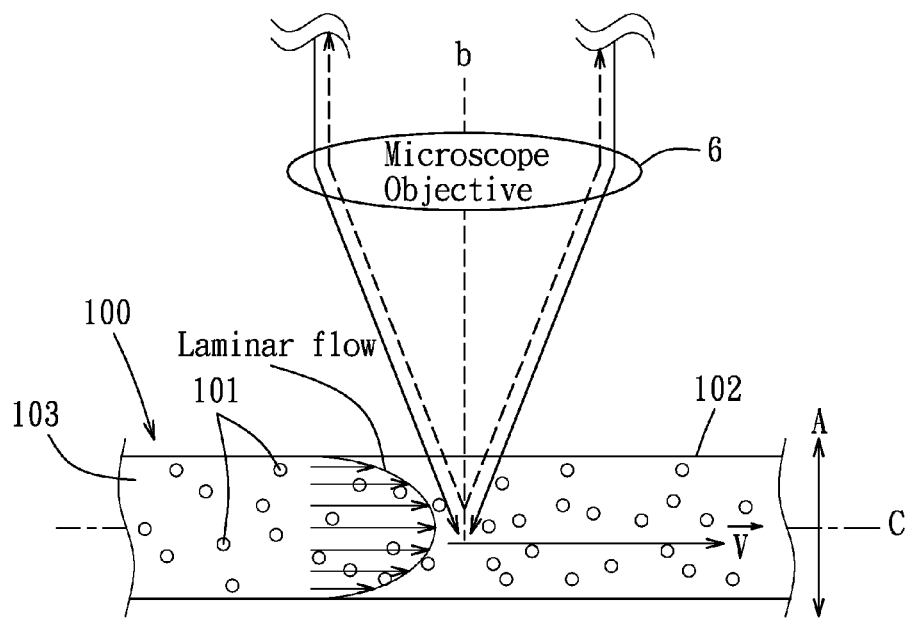
FIG. 5b is a fragmentary schematic view of the preferred embodiment when laminar flow profile within a flow tube is measured.

Preferably, the localized dynamic light scattering measurement system further includes a three-dimensional translation stage (not shown) adapted for supporting and moving the flow tube in a direction (A) shown in FIG. 5b to change the radial distance from zero to an inner radius of the capillary tube 102 such that the fluid flow velocities corresponding respectively to different radial distances ranging from zero to the inner radius of the capillary tube 102 are obtained by the signal processing unit 9, thereby obtaining a laminar flow profile within the capillary tube 102.

Figure 6:
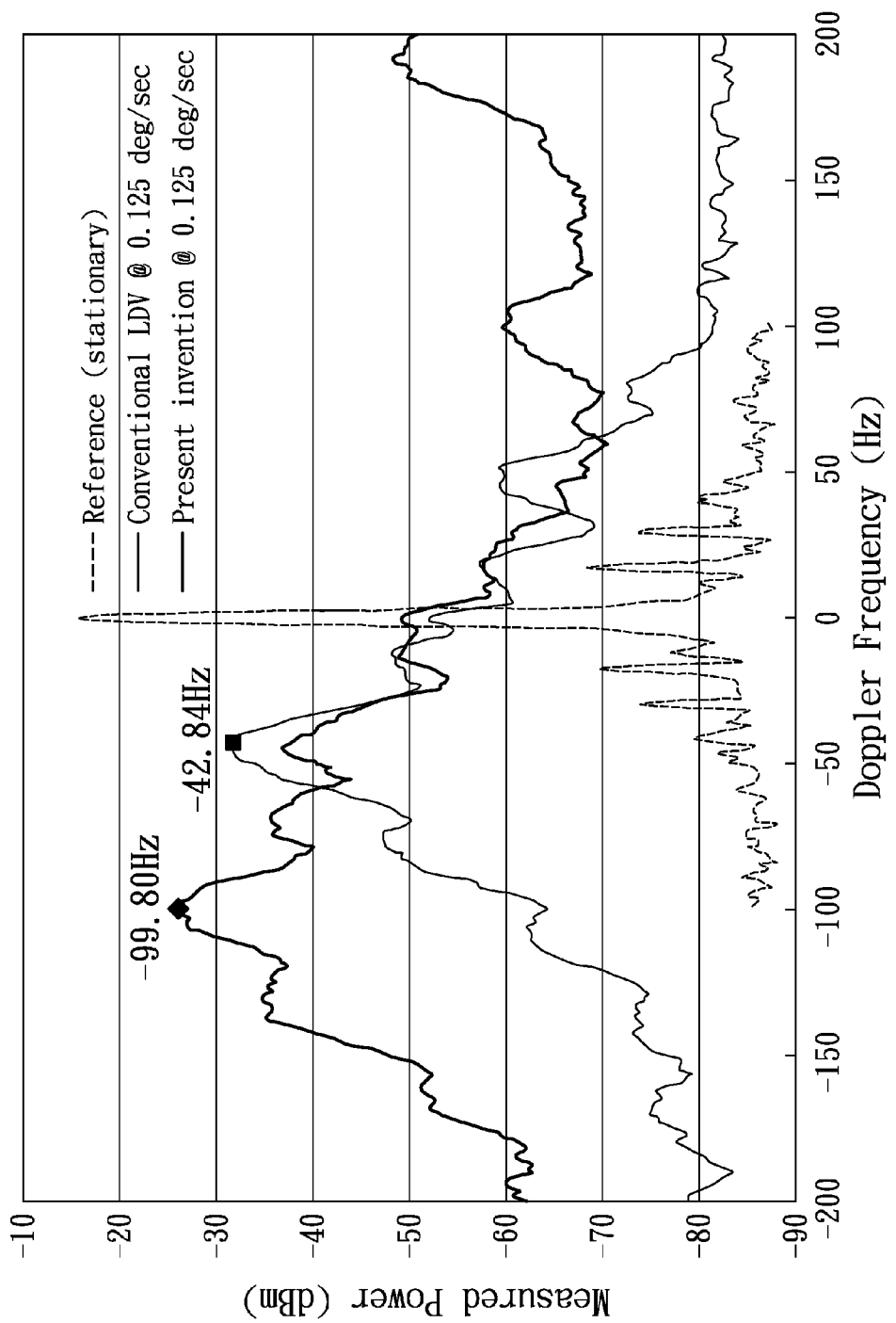
FIG. 6 is a measured power spectrum plot of experimental Doppler shift measurement results illustrating sensitivity comparison between the preferred embodiment and a conventional LDV.

FIG. 6 is a measured power spectrum plot of experimental Doppler shift measurement results illustrating sensitivity comparison between the preferred embodiment and a conventional LDV. In this experiment, the preferred embodiment and the conventional LDV simultaneously measure Doppler shift induced by turning the rotation stage in the first experiment at a fixed rotational speed of 0.125 deg/s. It can be seen from FIG. 6 that, at identical rotational speed setting, the preferred embodiment has higher Doppler shift measurement than the conventional LDV. The Doppler shift measurement is −99.80 Hz relative to zero Doppler frequency as the reference by using the preferred embodiment, and −42.84 Hz shift by using the conventional LDV. From the measurement, the sensitivity of the preferred embodiment is actually slightly more than twice of that of the conventional LDV.

If the object 100 is a sample that contains a plurality of nanoparticles in suspension undergoing Brownian motion, the power spectrum data generated by the spectrum analyzer 91 of the signal processing unit 9 includes a normalized power spectrum with a Lorentzian spectrum width, which is directly proportional to the diffusion coefficient of the Brownian particles and is inversely proportional to the particle size. The autocorrelation data generated by the autocorrelator 93 of the signal processing unit 9 includes an autocorrelation function in the form of an exponential time decay function, which indicates a characteristic time of the autocorrelation function inversely proportional to diffuse coefficient of the nanoparticles. The measurement data obtained by the processor 92 of the signal processing unit 9 includes an average size of the nanoparticles that is determined based on the Lorentzian spectrum width of the normalized power spectrum or the characteristic time of the autocorrelation data. In a third experiment of particle size measurement for various samples with different sizes made by the preferred embodiment using measured power spectrums, the samples includes several samples of polystyrene particles each having different particle diameter, such as 40 nm, 50 nm, 100 nm, 200 nm, 350 nm, 500 nm, and 1 μm, and a sample of 20 nm gold nanoparticles. In addition, in order to ensure the 180-degree reverse backscattered light intensity from smaller particles is sufficient for measurement, the two-frequency laser source 1 is required to have higher output power of 5 mW in this experiment. Table 3 shows theoretical data and experimental results, along with the parameters and constants used for calculations. From Table 3, some of the measured (calculated) particle size data do not agree with the nominal particle sizes provided by the manufacturer because each sample has a size distribution around its nominal size.

TABLE 3

| Boltzmann constant | Temperature | Viscosity of water | Laser wavelength | Refractive index of water | Angle between probe beams |
|---|---|---|---|---|---|
| 1.3806504E−23 | 298 K | 0.891 mPa · s | 633 nm | 1.33172 | 27.22 degree |

| Nominal particle size (nm) | Theoretical spectrum width (Hz) | Measured spectrum width (Hz) | Theoretical diffusion coefficients | Measured diffusion coefficients | Measured particle size (nm) |
|---|---|---|---|---|---|
| 20 | 10901 | 11297 | 7.70E−11 | 1.02E−10 | 19.3 |
| 40 | 5450 | 5657 | 3.85E−11 | 5.09E−11 | 38.5 |
| 50 | 4360 | 3726 | 3.08E−11 | 3.35E−11 | 58.5 |
| 100 | 2180 | 2043 | 1.54E−11 | 1.84E−11 | 106.7 |
| 200 | 1090 | 1111 | 7.70E−12 | 9.99E−12 | 196.3 |
| 350 | 625 | 745 | 4.40E−12 | 6.70E−12 | 292.6 |
| 500 | 437 | 468 | 3.08E−12 | 4.21E−12 | 465.8 |
| 1000 | 218 | 228 | 1.54E−12 | 2.05E−12 | 955.9 |

Due to the interception of two orthogonal linearly polarized first and second incident beams onto an object to be measured, and the selectivity of orthogonal linearly polarized 180-degree reverse backscattered signal beams, this embodiment presents the sectioning image ability with a few microns axial resolution based on the dynamical light scattering measurement.

Figure 7:
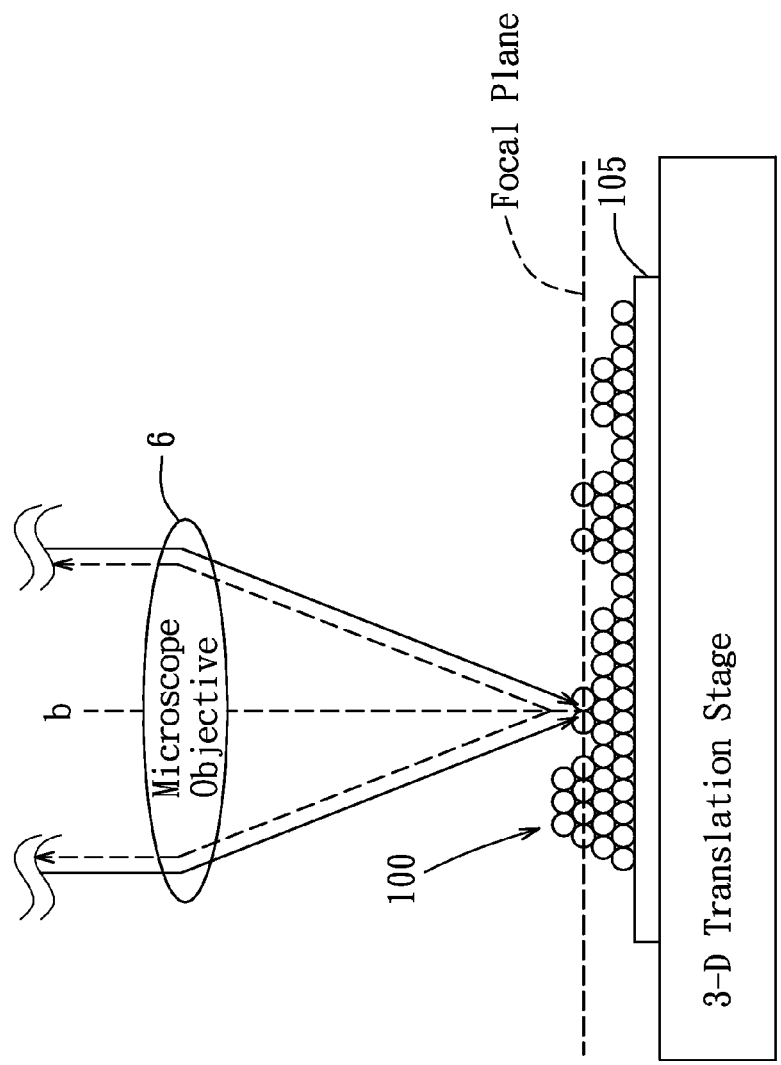
FIG. 7 is a fragmentary schematic view of the preferred embodiment when particles on a slide are measured.

Referring further to FIG. 7, if the object 100 is a sample that contains small particles placed on a slide 105, the signal processing unit 9 measures the intensity of the heterodyne interference signal while the particles are translated within a focal plane of the focusing lens unit 6 such that a localized two-dimensional sectioning image is acquired in accordance with the intensity of the heterodyne interference signal measured by the signal processing unit 9.

In sum, since the localized dynamic light scattering measurement system of the present invention utilizes the dual-polarization differential heterodyne method, when used as a LDV, without the AOMs 83 for frequency modulation in the prior art, configuration of the localized dynamic light scattering measurement system is relatively simple. In addition, since the amount of Doppler shift detected by the localized dynamic light scattering measurement system of the present invention is more than twice that detected by the conventional system using differential Doppler heterodyne technique, higher detection sensitivity can be achieved in the present invention. Furthermore, due to the presence of the beam displacer 4 and the iris 3, good localization in an axial direction can be simply achieved by using the polarization and spatial coherence gates created by the beam displacer 4 and the iris 3 without doing stringent alignment. In addition, only desired signal beams, i.e., the orthogonal linearly polarized 180-degree reverse backscattered signal beams, are selected from the scattered signal beams from an object to be measured using the combination of the beam displacer 4 and the iris 3, thereby effectively filtering out unwanted scattering photons so as to improve the selectivity of the desired signal. Moreover, since localization performance is improved, sectioning image capability is thus attained.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A localized dynamic light scattering measurement system comprising:

a two-frequency laser source for producing an input laser beam propagating along an optical axis and composed of orthogonal linearly polarized first and second beam components with slightly different frequencies;

a beam splitter disposed on the optical axis for transmitting a portion of the input laser beam produced by said two-frequency laser source such that the portion of the input laser beam transmitted by said beam splitter serves as an incident beam;

a beam displacer for splitting the incident beam into orthogonal linearly polarized first and second output beams corresponding respectively to the orthogonal linearly polarized first and second beam components, the orthogonal linearly polarized first and second output beams being parallel to the incident beam and being spaced apart from each other by a predetermined spacing upon exiting said beam displacer;

a focusing lens unit for focusing the orthogonal linearly polarized first and second output beams onto an object to be measured and collecting light backscattered from the object upon the orthogonal linearly polarized first and second output beams striking the object;

an iris disposed between said beam splitter and said beam displacer, and having an opening aligned with the optical axis for permitting the incident beam to pass through to limit a spot size of the incident beam;

wherein said beam displacer serving as a polarization gate cooperates with said iris serving as a spatial filter gate to collect and recombine scattering beams each reversely backscattered at 180 degrees from the object and corresponding to a specific portion of the light collected by said focusing lens unit, so as to form a signal beam to be detected that passes through said opening in said iris;

a polarizer for polarizing the signal beam from said iris to produce, along a polarization axis of said polarizer, first and second polarization components with common polarization;

a photo detecting unit receiving the first and second common polarization components from said polarizer to detect and generate a heterodyne interference signal associated with the first and second common polarization components, and converting the heterodyne interference signal into an electrical signal; and a signal processing unit connected electrically to said photo detecting unit for receiving the electrical signal therefrom, said signal processing unit being operable to analyze the electrical signal received thereby to generate power spectrum data and autocorrelation data corresponding to the heterodyne interference signal and obtain measurement data on the object based on the power spectrum data or the autocorrelation data.

2. The localized dynamic light scattering measurement system as claimed in claim 1, wherein an assembly of said beam displacer and said iris blocks unwanted scattering beams corresponding to the remaining of the light collected by said focusing lens unit.

3. The localized dynamic light scattering measurement system as claimed in claim 1, wherein the scattering beams respectively propagate in 180-degree reverse directions of the orthogonal linearly polarized first and second output beams, are coaxially recombined by said beam displacer after passing said beam displacer, and pass through said opening in said iris to form the signal beam.

4. The localized dynamic light scattering measurement system as claimed in claim 1, wherein said focusing lens unit includes a microscope objective.

5. The localized dynamic light scattering measurement system as claimed in claim 1, wherein said beam displacer is a uniaxial birefringence crystal prism.

6. The localized dynamic light scattering measurement system as claimed in claim 1, wherein said photo detecting unit includes a photomultiplier tube as a photodetector.

7. The localized dynamic light scattering measurement system as claimed in claim 1, wherein said signal processing unit includes:
   a spectrum analyzer connected electrically to said photo detecting unit for receiving the electrical signal therefrom, said spectrum analyzer being operable to analyze the electrical signal to generate the power spectrum data corresponding to the heterodyne interference signal;
   an autocorrelator connected electrically to said photo detecting unit for receiving the electrical signal therefrom, said autocorrelator being operable to analyze the electrical signal to generate the autocorrelation data corresponding to the heterodyne signal; and
   a processor connected electrically to said spectrum analyzer and said autocorrelator for receiving the power spectrum data and the autocorrelation data therefrom, said processor being operable to obtain measurement data on the object based on the power spectrum data from said spectrum analyzer and the autocorrelation data from said autocorrelator.

8. The localized dynamic light scattering measurement system as claimed in claim 1, wherein, when said localized dynamic light scattering measurement system is used as a laser Doppler velocimeter, the power spectrum data generated by said signal processing unit includes a Doppler shifted spectrum with a Doppler frequency.

9. The localized dynamic light scattering measurement system as claimed in claim 8, wherein, when the object is a solid sample, the measurement data obtained by said signal processing unit includes a moving speed of the object in a direction perpendicular to a bisector of the orthogonal linearly polarized first and second output beams focused by said focusing lens unit, the moving speed of the object being determined based on the Doppler frequency of the Doppler shifted spectrum.

10. The localized dynamic light scattering measurement system as claimed in claim 8, wherein, when the object is a flow tube that contains small particles in liquid suspension filled in a transparent capillary tube, the measurement data obtained by said signal processing unit includes a fluid flow velocity in the flow tube along a direction of a difference vector between a first incident wave vector corresponding to the first output beam and a second incident wave vector corresponding to the second output beam, the fluid flow velocity in the flow tube being determined based on the Doppler frequency of the Doppler shifted spectrum.

11. The localized dynamic light scattering measurement system as claimed in claim 1, wherein, when the object is a sample that contains nanoparticles in suspension undergoing Brownian motion:
   the power spectrum data generated by said signal processing unit includes a normalized power spectrum with a Lorentzian spectrum width;
   the autocorrelation data generated by said autocorrelator includes an autocorrelation function in the form of an exponential time decay function, which indicates a characteristic time of the autocorrelation function inversely proportional to diffuse coefficient of the nanoparticles; and
   the measurement data obtained by said signal processing unit includes an average size of the nanoparticles that is determined based on the Lorentzian spectrum width of the normalized power spectrum or the characteristic time of the autocorrelation function.

12. The localized dynamic light scattering measurement system as claimed in claim 1, wherein, when the object is a sample that contains small particles, said signal processing unit measures the intensity of the heterodyne interference signal while the particles are translated within a focal plane of said focusing lens unit such that a localized two-dimensional sectioning image is acquired in accordance with the intensity of the heterodyne interference signal measured by said signal processing unit.

* * * * *